United States Patent [19]

Maliga et al.

[11] Patent Number: 5,451,513
[45] Date of Patent: Sep. 19, 1995

[54] METHOD FOR STABLY TRANSFORMING PLASTIDS OF MULTICELLULAR PLANTS

[75] Inventors: Pal Maliga; Zora S. Maliga, both of East Brunswick, N.J.

[73] Assignee: The State University of New Jersey Rutgers, Piscataway, N.J.

[21] Appl. No.: 111,398

[22] Filed: Aug. 25, 1993

Related U.S. Application Data

[63] Continuation of Ser. No. 518,763, May 1, 1990, abandoned.

[51] Int. Cl.$^6$ .................. C12N 15/82; C12N 15/90; C12N 15/65; A01H 5/00
[52] U.S. Cl. .................. 435/172.3; 435/172.1; 435/240.4; 435/320.1; 800/205; 935/30; 935/52; 935/84
[58] Field of Search .............. 435/320.1, 172.1, 172.3, 435/240.4; 800/205; 935/30, 52, 84

[56] References Cited

FOREIGN PATENT DOCUMENTS 0251654 1/1988 European Pat. Off. ..... C12N 15/00

OTHER PUBLICATIONS

Boynton et al 1988 Science 240: 1534–1538.
Blowers et al 1989 (Jan.) Plant Cell 1: 123–132.
DeBlock et al 1985 EMBO Journal 4 (6): 1367–1372.
Fox et al 1988 Proc Natl Acad Sci USA 85: 7288–7292.
Daniell et al 1987 Proc Natl Acad Sci USA 84: 6349–6353.
Daniell et al 1990 (Jan.) Proc Natl Acad Sci USA 87: 89–92.
Zchwarz et al 1980 Nature 283: 739–742.
Moazed et al 1987 Nature 327: 389–394.
Fromm et al 1987 EMBO Journal 6 (11): 3233–3237.
Shinozaki et al 1986 EMBO Journal 5 (9): 2043–2049.
Moll et al 1990 (April) Mol Gen Genet 221: 245–250.
Svab et al 1990 (Nov.) Proc Natl Acad Sci USA 87: 8526–8530.
Vancanneyt, G. et al. (1990) Construction of an intron–containing marker gene: splicing of the intron in transgenic plants and its use in monitoring early events in *Agrobacterium*–mediated plant transformation. Mol. Gen. Genet. 220:245–250.
Svab, Z. et al. (1990) Aminoglycoside 3"–adenyltransferase confers resistance to spectinomycin in *Nicotania tabacum*. Plant Molecular Biology 14:197–205. (Feb).
Groning, B. R., et al. (1990), Replicative form DNA of abuliton mosaic virus is present in plastids. Mol. Gen. Genet. 220:485–488.

*Primary Examiner*—Patricia R. Moody
*Attorney, Agent, or Firm*—Janet E. Reed

[57] ABSTRACT

This invention provides methods for obtaining a plant cell of a multicellular plant, the plastids of which cell have been stably transformed by a foreign DNA of interest. These methods employ selectable markers some of which are nonlethal, some of which are designed to insert into the plastid genome and some of which are designed to be expressible only from the plastid genome and not from the nuclear genome. This invention also provides cells and multicellular plants the plastids of which have been stably transformed by a foreign DNA of interest.

13 Claims, 6 Drawing Sheets

METHOD FOR STABLY TRANSFORMING PLASTIDS OF MULTICELLULAR PLANTS

This application is a continuation of U.S. Ser. No. 07/518,763, filed May 1, 1990 now abandoned.

BACKGROUND OF THE INVENTION

Throughout this application various publications are referenced by citations within parentheses the complete cites for which may be found at the end of the specification immediately preceding the claims. The disclosures of these publications in their entireties are hereby incorporated by reference into this application in order to more fully describe the state of the art to which this invention pertains.

Transgenic plants are widely used to study nuclear gene function and regulation and to improve agronomically important crop plants (Benfey and Chua, 1989; Weising, et al., 1988). Routine application of the transgenic technology is made feasible by the alternative methods developed for the transformation of the nuclear genome of higher plants. However, the transgenic technology has not been applied yet to the genomes of the cytoplasmic organelles, plastids and mitochondria of higher plants.

The size of plastid DNA (ptDNA) in higher plants is in the range of 120 kb to 160 kb (Palmer, 1985), and encodes the genes involved in plastid maintenance and photosynthesis. By now three plastid genomes have been sequenced, including that of Nicotania tabacum (Shinozaki et al. 1986). In addition to photosynthesis, plastids serve as the compartment for amino acid biosynthesis and lipid biosynthesis (Boyer et al., 1989). Most if not all the genes involved are encoded by the nucleus. The enzymes encoded by nuclear genes are synthesized on cytoplasmic ribosomes, and are subsequently transported into the plastids. Expression and accumulation of nuclear gene products and of plastid gene products is coordinated (Gruissem, 1989; Zurawski and Clegg, 1987).

Formation of stable transformed plastid genomes requires integration of the transforming DNA by recombination. That recombination is a mechanism contributing to the evolution of plastid genome is evident when comparing genomes of different plant species. Also, continued recombination through the plastid inverted repeat has been described (Palmer 1985). It has also been shown that intergenomic plastid recombination occurs in heteroplastidic cells obtained by protoplast fusion (Medgyesy et al. 1985; Thanh and Medgyesy, 1989), and is extensive (Fejes et al., 1990).

Introduction and stable integration of exogenous DNA has been reported recently in the plastid genome of a unicellular alga, Chlamydomonas reinhardtii (Boynton et al. 1988; Blowers et al. 1989). Initial success in transforming the plastid genome of Chlamydomonas by Boynton et al. (1988) was made possible by the development of a microprojectile DNA delivery system based on a particle gun that delivers DNA-coated tungsten microprojectiles into the cell. In addition, a powerful selection scheme was applied that relied on complementing nonphotosynthetic deletion mutants. Subsequently, Blowers et al. (1989) have shown that the Chlamydomonas plastid genome can be expanded by integrating the coding sequence of an E. coli enzyme, neomycin phosphotransferase. Transformation of the psbA gene encoding the D1 reaction center polypeptide of photosystem II, and of the 16s rRNA gene conferring resistance to streptomycin and spectinomycin was reported by Boynton et al., 1990. The psbA and rRNA genes in Chlamydomonas are located in the repeated region. In the transformed clones the repeated regions were identical indicating that transformation was followed by copy correction. The frequency of transformation was as high as $1.4 \times 10^{-4}$. Reducing the number of chloroplast genomes five to seven fold by growing the recipient cells on 5-fluorodeoxyuridine prior to transformation increased the frequency of transformation 20 to 280 fold (Boynton et al., 1990).

In higher plant chloroplasts, only transient expression of introduced DNA has been claimed. DNA uptake and transient expression by isolated cucumber etioplasts of the large and small subunits of ribulose bisphosphate carboxylase/oxygenase of Anacystis nidulans, or of the E. coli enzyme, chloramphenicol acetyltransferase (CAT), has been reported (Daniell and McFadden 1987). The 5' end of the psbA (pea), and rbcL (maize) plastid genes were fused with the CAT gene. Transient expression of the constructs in chloroplasts of cultured tobacco cells has been claimed by Daniell, et al. (1990) after biolistic delivery. Some of the vectors contained replication origins from ptDNA. CAT activity was sustained longer when the replicon origins were present. CAT activity, however, was not shown to be localized in chloroplasts. CAT activity, therefore, may be the result of expression in the nucleus, since plastid gene promoters are known to support transcription initiation in the nucleus (Cornelissen and Vandewiele, 1989). European Application No. 87305573.5, filed Jun. 23, 1987, by M. C. Cannon and F. C. Cannon, describes a method for producing a plant whose cells express a desired gene by inserting the desired gene into plastids of a plant cell. However, this application does not suggest a method for stably transforming plastids using nonlethal selection. Transformation of plastids in higher plants was claimed after Agrobacterium-mediated transformation of N. tabacum (DeBlock et al. 1985). A CAT gene was engineered for expression in the nucleus, and transgenic clones were selected for resistance to 10 µg/ml chloramphenicol. The authors claim that there was fortuitous integration of the CAT gene into the ptDNA and expression from a plastid promoter. The line was reportedly unstable, and the authors' claims have not been confirmed.

There are several differences between the Chlamydomonas system and higher plants that maybe relevant for successful transformation of plastids. Two of these are discussed below. The number of plastids, and the number of plastid genomes per cell is much lower in Chlamydomonas than in Nicotiana. Chlamydomonas contains a single plastid. Every plastid carries up to 80 identical plastid genomes (Harris, 1989). Nicotiana tabacum cells contain a variable number of plastids, about 100 in leaf cells, and 12 to 14 in meristematic cells and dedifferentiated tissue culture cells (Thomas and Rose, 1983). In a study with cultured cells the number of plastid genome copies was estimated to be 3,000 to 12,000 per cell (Cannon, et al., 1985; Yasuda, et al., 1988). Clearly, there are many more plastid genome copies in Nicotiana than in Chlamydomonas. Another important difference is that Chlamydomonas cells are grown photoautotrophically which allows a stringent selection for photosynthetic ability, that is, functional plastids. Photoheterotrophic culture in higher plants, however, reduces the stringency of selection for functional plastids, a requirement for transformation with all the proven methods including Agrobacterium-mediated transformation (Weising et al. 1988), electroporation (Fromm et al 1986), calcium phosphate coprecipitation (Krens et al. 1982) and transformation by high-velocity microprojectiles (Klein et al. 1988a), and polyethylene glycol treatment (Negrutiu, et al, 1987).

Given the large number of plastid genomes in plant cells (Possingham and Lawrence, 1983; Palmer, 1985) the ability to select for the transformed genome in culture is a key element in achieving plastid transformation. Available markers are reviewed below. Since most of the selectable plastome markers have been developed through cell culture, it is not surprising that most plastome markers are available in *Nicotania tabacum* and *Nicotiana plumbaginifolia,* two species that are easy to grow in cell culture and to subsequently regenerate into plants. Resistance to inhibitors of protein synthesis, conferred by mutation in the plastid 16S rRNA and 23S rRNA genes, are the most readily available markers. The list of markers includes resistance to streptomycin (Maliga et al. 1973; Etzold et al. 1987; Fromm et al. 1989), spectinomycin (Fromm et al. 1987) and lincomycin (Cseplo and Maliga 1984; Cseplo et al. 1988) which are the equivalent rRNA gene mutation used for transformation in Chlamydomonas (Harris et al. 1989). These mutants have been characterized genetically, after plant regeneration, and at the DNA sequence level. Higher plant cells in photoheterotrophic culture respond to these drugs by bleaching and retarded growth, but not cell death. Bleaching in cell culture is not lethal because culture medium containing sucrose dispenses with the requirement for photosynthesis. Differentiation in culture of resistant mutants from the sensitive parental type is based on greening and faster growth. Chlamydomonas cells are grown photoautotrophically, hence the same markers are lethal. In more detail, mutant line SR1 (Maliga et al. 1973; Etzold et al. 1987), SPC1 and SPC2 (unpublished) carry mutations in the 16S rDNA that confer resistance to streptomycin, spectinomycin, and both drugs, respectively. In the SR1 line a change of C to A in the 16S rDNA at position 860 confers resistance to streptomycin (Etzold et al. 1987). The SR1 line is sensitive to spectinomycin. In the SPC1 line mutation A1138 to C in the 16S rDNA confers resistance to spectinomycin. This line is sensitive to streptomycin. The SPC2 line is a derivative of the SR1 streptomycin resistant line, and was selected for spectinomycin resistance. A second rDNA mutation, a change of C to U at position 1139, confers resistance to spectinomycin. The line is resistant to high levels of streptomycin and spectinomycin (500 ug each) and resistance to both drugs is simultaneously expressed (unpublished results of Zora Svab). Mutations similar to those in the SPC1 and SPC2 lines are known in Chlamydomonas (Harris et al. 1989). Plastome mutants resistant to triazine herbicides, have also been obtained in cultured Nicotiana cells. Triazine herbicides inhibit photosynthesis by interruption of electron flow at the acceptor of photosystem II. Selection was feasible in cultures when lowering the concentration of sucrose in the medium made cellular proliferation partially dependent on photosynthesis (photomixotrophic cultures; Cseplo, et al., 1985; Sato, et al., 1988). Selection for resistance to this class of herbicides is also a nonlethal color selection. The resistant clones are identified by their green color (Cseplo, et al., 1985). A mutation in two of the lines was localized to the psbA gene (Pay et al. 1988; Sato et al. 1988). Similar mutant have been found in higher plants under field conditions (Maliga, et al. 1990), and isolated in Chlamydomonas (Erickson, et al., 1985). Naturally occurring resistance to tentoxin is also plastome-encoded (Durbin and Uchytil 1977). Pigment deficiency caused by plastome mutation is frequent. It does not appear to be a useful marker in culture. Pigment mutation in combination with antibiotic resistance mutations, however, proved important in recovering a recombinant plastid genome (Medgyesy et al. 1985).

The present invention provides a method for stable transformation of the plastids of higher plants. Others have attempted to obtain stable plastid transformation in higher plants, but without success.

SUMMARY OF THE INVENTION

This invention provides a method for obtaining a plant cell of a multicellular plant, the plastids of which cell have been stably transformed by a foreign DNA of interest, which comprises transforming the plastids of cells of the multicellular plant with the foreign DNA of interest and with plastid DNA which encodes at least one nonlethal selectable phenotype, expression of which phenotype by a cell occurs only when substantially all of the plastids of such cell have been transformed; selecting for cells which express such phenotype; and thereby obtaining the plant cell the plastids of which cell have been stably transformed by the foreign DNA of interest.

This invention also provides a plant cell the plastids of which cell have been stably transformed by a foreign DNA of interest by transforming them with the foreign DNA of interest and with plastid DNA which encodes at least one nonlethal selectable phenotype, expression of which phenotype by a cell occurs only when substantially all of the plastids of such cell have been transformed; selecting for cells which express such phenotype; and thereby obtaining the plant cell the plastids of which cell have been stably transformed by the foreign DNA of interest.

This invention further provides a method for obtaining a multicellular plant, the plastids of which have been stably transformed by a foreign DNA of interest, which comprises obtaining a plant cell the plastids of which cell have been stably transformed by the foreign DNA of interest by transforming the plastids of cells of the multicellular plant with the foreign DNA of interest and with plastid DNA which encodes at least one nolnethal selectable phenotype, expression of which phenotype by a cell occurs only when substantially all of the plastids of such cell have been transformed, selecting for cells which express such phenotype, and thereby obtaining the plant cell the plastids of which cell have been stably transformed by the foreign DNA of interest; and regenerating the multicellular plant the plastids of which have been stably transformed by a foreign DNA of interest from the plant cell so obtained.

This invention provides the multicellular plant obtained by the method described supra.

This invention also provides a multicellular plant the plastids of which have been stably transformed by a foreign DNA of interest.

This invention provides a method for obtaining a plant cell of a multicellular plant, the plastids of which cell have been transformed by a foreign DNA of interest, which comprises transforming the plastids of cells of the multicellular plant with the foreign DNA of interest and with DNA which encodes a nonlethal selectable phenotype expression of which phenotype by a cell occures only when substantially all of the plastids of such cell have been tranformed, and at least one plastid intron which cannot be processed in the nucleus thereby preventing expression of the selectable phenotype by the nuclear genome in the cytoplasm, selecting for cells which express the selectable phenotype, and thereby obtaining the plant cell, the plastids of which cell have been transformed by the foreign DNA of interest.

This invention provides a method for obtaining a plant cell of a multicellular plant, the plastids of which cell have been transformed by a foreign DNA of interest, which comprises transforming the plastids of cells of the multicellular plant with the foreign DNA of interest and with DNA from which the translation initiation signal has been deleted and which encodes a nonlethal selectable phenotype expression of which phenotype by a cell occurs only when substantially all of the plastids of such cell have been tranformed, and trans splicing signals which cannot be processed in the nucleus thereby preventing expression of the selectable phenotype in the nuclear genome, selecting for cells which express the selectable phenotype, and thereby obtaining the plant cell, the plastids of which cell have been transformed by the foreign DNA of interest.

This invention provides a method for obtaining a multicellular plant which has been transformed by a foreign DNA of interest which comprises stably transforming the plastids of the cells of the multicellular plant to insert DNA which encodes a nonlethal selectable phenotype and delete a gene in the absence of which the cells survive in culture but do not regenerate viable plants, selecting for cells which express such phenotype, inserting into the plastids of the resulting cells a microgenome which comprises DNA encoding the gene in the absence of which the cells survive in culture but do not regenerate viable plants and the foreign DNA of interest, and regenerating the multicellular plant which has been transformed by a foreign DNA of interest from the plant cells the plastids of which contain the microgenome.

This invention provides a method for obtaining a plant cell of a multicellular plant which has been transformed by a foreign DNA of interest, which comprises stably transforming the plastids of the cells of the multicellular plant to insert DNA which encodes a first nonlethal selectable phenotype and delete a gene in the absence of which the cells cannot survive in culture, and also inserting a microgenome which comprises DNA encoding the gene in the absence of which the cells cannot survive in culture and a second nonlethal selectable phenotype, selecting for cells which express the first phenotype, inserting into the plastids of the resulting cells a second microgenome which comprises DNA encoding a third nonlethal selectable phenotype and the foreign DNA of interest, selecting for cells which express the third phenotype and do not express the second phenotype, and thereby obtaining the plant cell which has been transformed by the foreign DNA of interest.

The Bluescript vector contains the 3.7 kb SacI-EcoRV fragment from the SPC2 ptDNA. The 16S rDNA is highlighted, and the relative position of streptomycin (str-1) and spectinomycin (spc-2) resistance mutations, and of the PstI linker (*), is shown. The 2.9 kb SalI fragment includes a region implicated in ptDNA replication (pt ori).

Figure 2A:
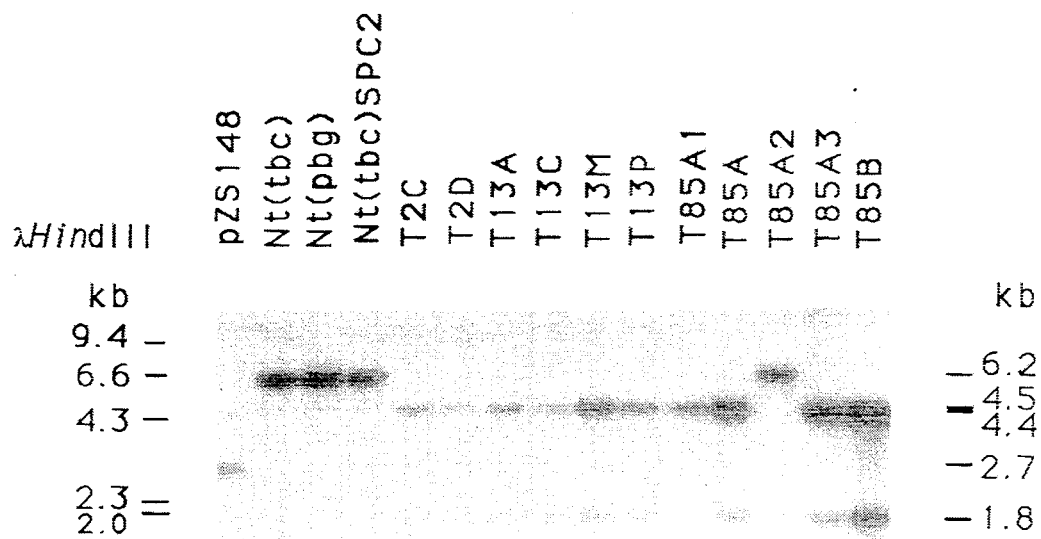

FIG. 2A. Southern probing of total cellular DNA to screen for the PstI marker.

Results of probing total cellular DNA are shown after digestion with PstI and HindIII restriction endonucleases. As controls, pZS148 plasmid DNA, and DNA of the Nt(tbc), Nt(pbg) and Nt(tbc)SPC2 lines were included.

Figure 2B:
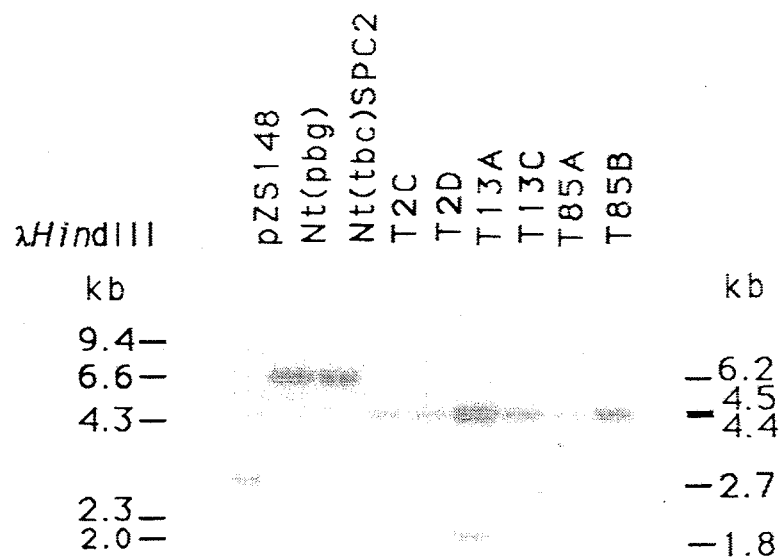

FIG. 2B. Southern probing of isolated plastid DNA to screen for the PstI marker.

Results of probing isolated plastid DNA are shown after digestion with PstI and HindIII restriction endonucleases. As controls, pZS148 plasmid DNA, and DNA of the Nt(tbc), Nt(pbg) and Nt(tbc)SPC2 lines were included.

Figure 2C:
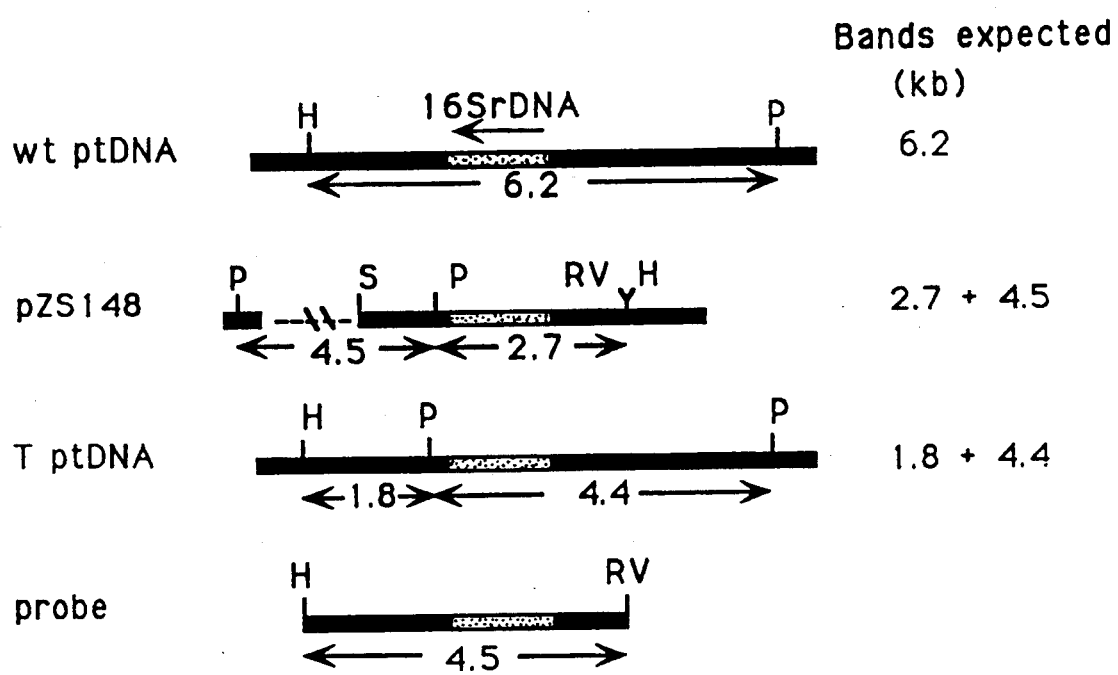

FIG. 2C. Physical map of the probed wild-type (wt) and transgenic (T) ptDNA shown in FIGS. 2A and 2B.

Physical map of the probed region of wild-type (wt) and transgenic (T) ptDNA, and the relative position of the probe, and of the 16S rDNA (highlighted) in pZS148 are shown. Expected sizes of hybridizing fragments are listed. Restriction endonucleases: EV, EcoRV; H, HindIII; P, PstI; S, SacI.

Figure 3A:
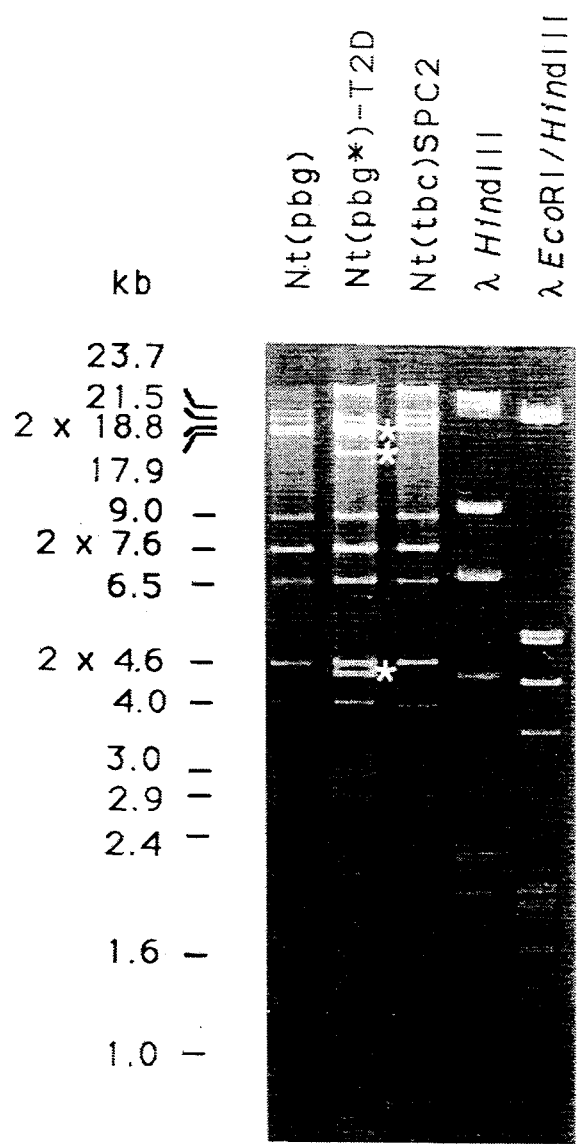

FIG. 3A. PstI fragment pattern of the Nt(pbg*)T2D plastid DNA indicates copy-correction for the region containing the PstI linker.

Purified plastid DNA was digested, and the fragments were separated in agarose gels. Lanes contain Nt(pbg), Nt(pbg)T2D, and Nt(tbc) ptDNA digests. Lambda DNA digested with the HindIII (H) or the HindIII/EcoRI (H,E) restriction endonucleases was run alongside to serve as molecular weight standards. The size of PstI fragments in the Nt(pgb) recipient are given. Note that the 18.8 kb and 18.9 kb fragments do not separate and are marked as a doublet. The novel 4.4 kb, 14.4 kb, and 19.3 kb fragments in the Nt(pgb*)T2D ptDNA are marked with an asterisk.

Figure 3B:
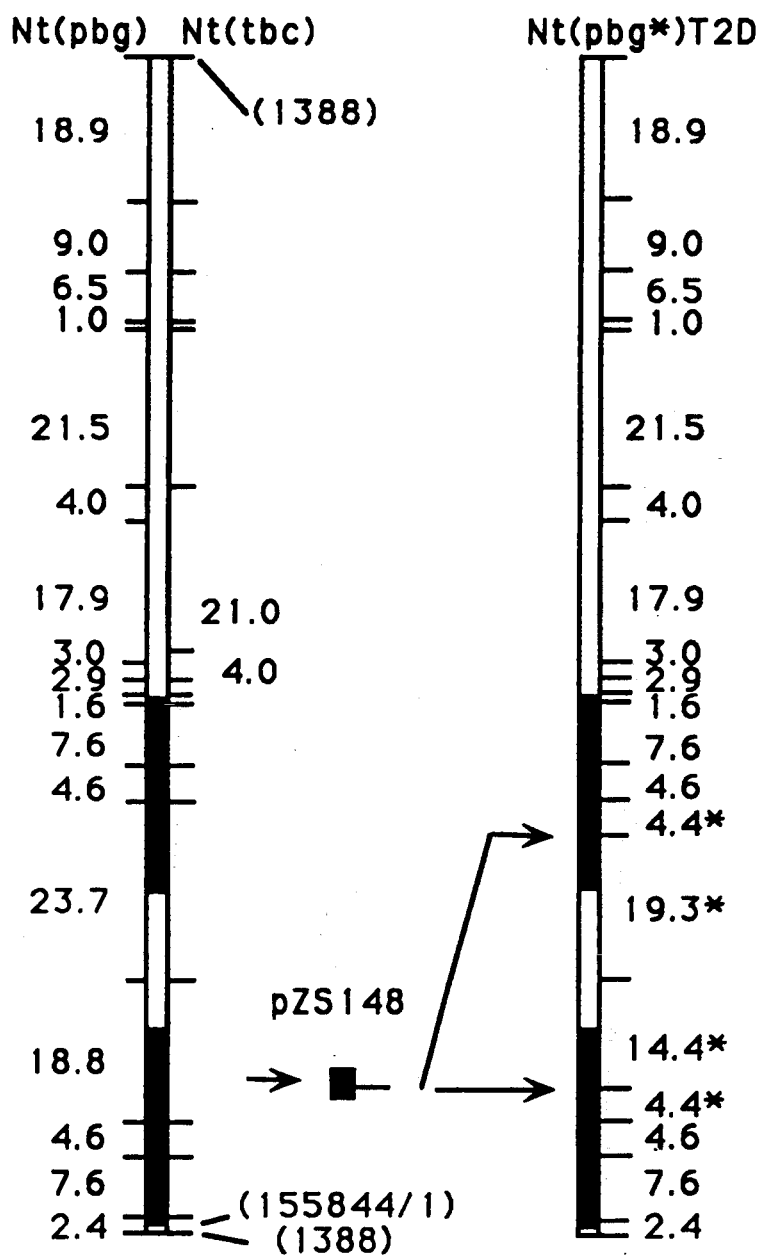

FIG. 3B. PstI map of plastid DNA from data shown in FIG. 3A.

The circular map was linearized at bp 1388 for convenience to include complete PstI fragments. Junction of bp 1 and bp 155844 are given in brackets. The sizes of fragments are given in kilobase pairs. The filled bars indicate repeated regions. Map position of the 3.7 kb 16S rDNA fragment, contained in plasmid vector pZS148, is shown. Note that the 23.7- and 18.8-kb Nt(pbg) fragments disappear due to the integration of the PstI linker. New 4.4-, 14.4-, and 19.3-kb fragments that form as a result are marked with an asterisk. with the HindIII (H) or the HindIII/EcoRI (H,E) restriction endonucleases was run alongside to serve as molecular weight standards. The size of PstI fragments in the Nt(pgb) recipient are given. Note that the 18.8 kb and 18.9 kb fragments do not separate and are marked as a doublet. The novel 4.4 kb, 14.4 kb, and 19.3 kb fragments in the Nt(pgb*)T2D ptDNA are marked with an asterisk. (B) PstI map of plastid DNA from data shown in FIG. 3A. The circular map was linearized at bp 1388 for convenience to include complete PstI fragments. Junction of bp 1 and bp 155844 are given in brackets. Size of fragments is given in kilobasepairs. Filled bar indicates repeated region. Map position of the 3.7 kb 16S rDNA fragment, contained in plastid vector pZS148, is shown. Arrows point to position of novel PstI site.

Figure 4:

FIG. 4. Antibiotic resistance phenotype in leaf callus. Nt [Nt(tbc)] and SPC2 [Nt(tbc)SPC2] are the wild type recipient, and the source of transforming spectinomycin and streptomycin resistant 16S rDNA, respectively. Nt-T2 [Nt(pbg*)T2D] is a transgenic clone, SPC1 [Nt(tbc)SPC1] is a control line which is resistent to spectinomycin but sensitive to streptomycin (P.M. and Z.S.M., unpublished results). Note that resistant leaves form green callus, and sensitive leaves form white callus. Plates contain 500 µg/ml spectinomycin dihydrochloride (Sp500), streptomycin sulfate (Sm500), or both antibiotic (Sp500/Sm500).

Figure 5:
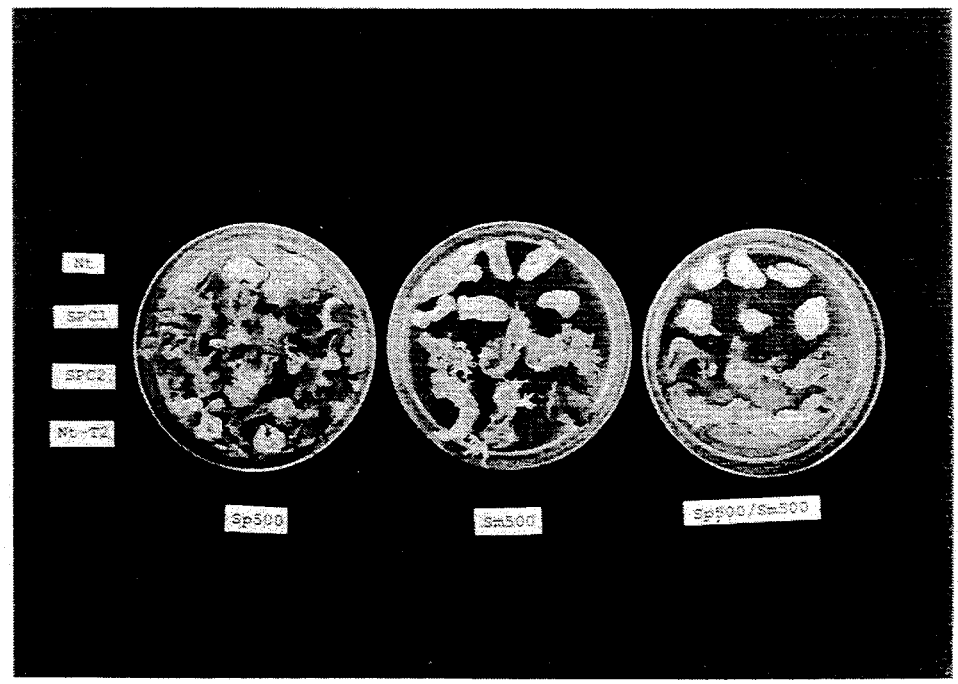

FIG. 5. Antibiotic resistance in the seed progeny of the transplastgenic line Nt (pbg) T2D. Seeds have been germinated on a selective medium containing spectinomycin and streptomycin. Note resistant (green), sensitive (white), and chimeric seedlings with green and white sectors.

DETAILED DESCRIPTION OF THE INVENTION

This invention provides a method for obtaining a plant cell of a multicellular plant, the plastids of which cell have been stably transformed by a foreign DNA of interest, which comprises transforming the plastids of cells of the multicellular plant with the foreign DNA of interest and with plastid DNA which encodes at least one nonlethal selectable phenotype, expression of which phenotype by a cell occurs only when substantially all of the plastids of such cell have been transformed; selecting for cells which express such phenotype; and thereby obtaining the plant cell the plastids of which cell have been stably transformed by the foreign DNA of interest. The plastid DNA may further comprise a plastid DNA replication site. The foreign DNA of interest and the plastid DNA may be self-contained or may be carried on a single DNA molecule or on separate DNA molecules, i.e. a single DNA molecule may comprise the foreign DNA of interest and the plastid DNA, or separate DNA molecules may comprise the foreign DNA of interest and the plastid DNA. When carried on separate DNA molecules, a high percentage of the DNA molecules cointegrate into the plastid genome, so that expression of the phenotype indicates that the foreign DNA has also been integrated.

The plant cell may be a cell from any multicellular plant, for example cells of trees used for their timber or fruit, field plants such as plants grown for grain, or any other plants. The plastids of these cells may be stably transformed with a foreign DNA of interest by the method described above, i.e., all the plastids of a given cell contain the foreign DNA and express the foreign DNA, and none of the plastids in the cell do not contain and express this DNA. The stability of transformation comes from this state, known as homoplasmy. Since no nontransformed plastids remain in a given cell, there is no possibility of reversion to a nontransformed state because there are no nontransformed plastids in the cell. The foreign DNA of interest used to transform the plant cell may be plastid DNA, or plant nuclear DNA, or heterologous DNA from any source from bacterial to mammalian DNA. Any method of transformation known in the art may be used in this method to get the DNA of interest into the plant cell. Once the DNA is in the cell, it will integrate into a plastid genome by homologous recombination. Because the selection technique employs plastid DNA encoding a nonlethal selectable phenotype, the DNA inserted will be targeted to the plastid genome. The homoplasmic state, wherein all the plastids in a cell integrate the foreign DNA, occurs as a result of the nonlethal selection system. Cells that do not contain enough transformed plastids survive. During the selection process, the transformed plastid genomes reproduce themselves. Eventually, almost all the plastids in a given cell will contain the transformed genome and the cell will express the selectable phenotype. The selection process is simply to pick cells which express the phenotype. This may be accomplished by tranforming a plant tissue such as a leaf. The leaf will then form dedifferentiated callus tissue, which will show the selectable phenotype. The selection process may also be performed using cells in tissue culture. Once the transformed cell has been selected, it is cultured and exposed to medium containing substances such as plant hormones which stimulate the cells to differentiate into whole plants. This is often done using callus cultures, which are easily stimulated to grow into plants by methods well known in the art.

Examples of methods of transforming are bombarding the cells of the multicellular plant with microprojectiles coated with the foreign DNA of interest and plastid DNA, agitation of the cells of the multicellular plant with beads coated with the foreign DNA of interest and plastid DNA; use of an *Agrobacterium tumefaciens* vector comprising the foreign DNA of interest and the plastid DNA; use of a geminivirus vector comprising the foreign DNA of interest and the plastid DNA; calcium phosphate precipitation of the foreign DNA of interest and the plastid DNA into protoplasts prepared from the cells of the multicellular plant; electroporation of the foreign DNA of interest and the plastid DNA into protoplasts prepared from the cells of the multicellular plant; and polyethylene glycol treatment to introduce the foreign DNA of interest and the plastid DNA into protoplasts prepared from the cells of the multicellular plant. The beads used in the agitation method are very fine and are suspended with DNA until coated. Agitation with beads gets the DNA through the plant cell wall without killing the cell. Examples of beads are glass beads and tungsten beads. Transformation with *Agrobacterium tumefaciens* or by calcium phosphate precipitation or electroporation are methods well known in the art. Polyethylene glycol precipitation is a method similar to calcium phosphate precipitation. Geminivirous vectors are useful for transformation. DNA of a germinivirous, the abutilon mosaic virus, has been shown to enter plastids.

An example of a nonlethal selectable phenotype is resistance to a photosystem II herbicide, such as a triazine herbicide, specifically the triazine herbicide atrazine. This phenotype not only provides nonlethal selection, but provides herbicide resistance. Resistant mutants in higher plants are available, but their fitness is reduced due to altered photosynthetic electron transport. Plastid mutations in Chlamydomonas have been developed that are resistant to photosystem II herbicides but have normal electron transport. Resistance to photosystemII herbicides such as atrazine, diuron, or DCMU based on mutations in the psbA plastid gene introduced into chloroplasts by in vitro mutagenesis of cloned genes and transformation yields higher plants that are resistant to photosystem II herbicides and have normal electron transport.

Another example of a nonlethal selectable phenotype is resistance to a substance which inhibits protein synthesis by the plastids, such that cells which have acquired the nonlethal selectable phenotype are selected for by contacting the cells with a substance which inhibits protein synthesis by the plastids. The plastid DNA encoding the nonlethal selectable phenotype may comprise 16S ribosomal DNA mutated to confer resistance to the effects of streptomycin, or to spectinomycin, or to both antibiotics simultaneously. In this example, the resulting nonlethal selectable phenotype is green pigmentation. Expression of heterologous genes that modify non-lethal antibiotics such as streptomycin or spectinomycin by phosphorylation, adenylation or acetylation also are suitable for non-lethal selection of transplastgenic clones.

This invention also provides a plant cell the plastids of which cell have been stably transformed by a foreign DNA of interest by transforming them with the foreign DNA of interest and with plastid DNA which encodes at least one nonlethal selectable phenotype, expression of which phenotype by a cell occurs only when substantially all of the plastids of such cell have been transformed, selecting for cells which express such phenotype, and thereby obtaining the plant cell the plastids of which cell have been stably transformed by the foreign DNA of interest. An example of a foreign DNA of interest is DNA which encodes a protein for production by the cell in a bioreactor, such as a protein of agronomic, medical, or industrial importance. Such proteins may be toxins that kill plant pests, or therapeutic proteins such as insulin, or proteins such as enzymes and other catalysts useful in industrial processes. The cells are grown in culture by methods well known in the art, and the protein produced is isolated from the culture medium or from the homogenized cells, by methods well known in the art.

One example of a plastid is a chloroplast, and one example of a multicellular plant is an agronomically important plant, such as *Nicotiana tabacum*. Examples of some foreign DNA of interest for this method which could be usefully inserted into a plant plastid genome are DNA which encodes herbicide resistance, DNA which encodes the ability to fix nitrogen, DNA which encodes increased photosynthetic capacity, DNA which encodes drought resistance, DNA which encodes salt tolerance, DNA which encodes resistance to extremes of temperature, DNA which encodes resistance to plant disease, and DNA which encodes resistance to plant pests, such as insects, nematodes, and protozoans. The nitrogenase enzyme which catalyzes nitrogen fixation is sensitive to oxygen. Therefore a plastid, which constitutes a compartment, is a good environment for the enzyme provided that the plastid is engineered not to evolve oxygen. When nitrogen fixing plastids are carried by a plant cell, normal plastids are also present in the same plant to ensure normal photosynthesis. Examples of herbicide resistance obtained by plastid transformation include overproduction of a herbicide target enzyme, such as resistance to glyphosate via overproduction of 5-enolpyruvylshikimate-3-phosphate synthase (pEPSPS), a nuclear gene (Comai et al., 1985; Shah et al., 1986). Another example is replacement with a mutant form of a target enzyme which is less sensitive to the herbicide, such as resistance to sulfonylurea (chlorsulfuron) and imidazolinone due to expression of mutant nuclear enzyme acetolactate synthase (ALS). EPSPS and ALS (Haughn et al., 1988; Lee et al., 1988) are nuclear encoded, chloroplast localized enzymes. Introduction of these genes into plastids results in synthesis of the protein in the compartment where it is normally found. The transit sequence that targets the cytoplasmic translation product must be removed when converting the resistant nuclear gene into a plastid gene for introduction into the plastid genome.

This invention further provides a method for obtaining a multicellular plant, the plastids of which have been stably transformed by a foreign DNA of interest, which comprises obtaining a plant cell the plastids of which cell have been stably transformed by the foreign DNA of interest by transforming the plastids of cells of the multicellular plant with the foreign DNA of interest and with plastid DNA which encodes at least one nonlethal selectable phenotype, expression of which phenotype by a cell occurs only when substantially all of the plastids of such cell have been transformed; selecting for cells which express such phenotype; and thereby obtaining the plant cell the plastids of which cell have been stably transformed by the foreign DNA of interest; and regenerating the multicellular plant the plastids of which have been stably transformed by a foreign DNA of interest from the plant cell so obtained.

This invention provides the multicellular plant obtained by the method described supra.

This invention also provides a multicellular plant the plastids of which have been stably transformed by a foreign DNA of interest. Examples of foreign DNA of interest are DNA which encodes herbicide resistance, DNA which encodes the ability to fix nitrogen, DNA which encodes increased photosynthetic capacity, DNA which encodes drought resistance, DNA which encodes salt tolerance, DNA which encodes resistance to extremes of temperature, DNA which encodes resistance to plant disease, and DNA which encodes resistance to plant pests, such as insects, nematodes, and protozoans, and DNA which encodes a protein which is isolated from the plant, specifically a protein of agronomic, medical, or industrial importance. The plant is then grown and harvested, and the protein is isolated by methods well known in the art from plant tissue, for example by pulverizing the plant tissue and extracting the protein from the pulverized plant tissue.

This invention provides a method for obtaining a plant cell of a multicellular plant, the plastids of which cell have been transformed by a foreign DNA of interest, which comprises transforming the plastids of cells of the multicellular plant with the foreign DNA of interest and with DNA which encodes a nonlethal selectable phenotype expression of which phenotype by a cell occures only when substantially all of the plastids of such cell have been tranformed, and at least one plastid intron which cannot be processed in the nucleus thereby preventing expression of the selectable phenotype by the nuclear genome in the cytoplasm, selecting for cells which express the selectable phenotype, and thereby obtaining the plant cell, the plastids of which cell have been transformed by the foreign DNA of interest. Gene replacement and insertion into the plastid genome requires selectable marker genes expressed under the control of plastid gene expression signals. To avoid the problem of expression in the nucleus, plastid introns are incorporated into the selective marker genes. Although some classes of plastid introns can be correctly spliced out in the nucleus, others cannot. This latter class of introns is useful to prevent nuclear expression of the inserted DNA. Insertion of an intron into a gene has been used to prevent expression in Agrobacterium so that expression occurs only in the plant nucleus (Vancanneyt et al., 1990). An example of this method uses a plastid intron which cannot be processed in the nucleus thereby preventing expression of the selectable phenotype by the nuclear genome in the cytoplasm and which comprises at least one translation termination signal and is inserted in the DNA which encodes a nonlethal selectable phenotype. In another example, the intron is inserted upstream of the DNA which encodes a nonlethal selectable phenotype. Another example of this method uses a plastid intron which cannot be processed in the nucleus thereby preventing expression of the nonlethal selectable phenotype by the nuclear genome in the cytoplasm and which comprises a translation initiation signal and a translation termination signal and is inserted at the 5' end of the DNA which encodes the nonlethal selectable phenotype upstream of a second translation initiation signal also inserted at the 5' end of the DNA which encodes the nonlethal selectable phenotype. Yet another example uses a plastid intron which cannot be processed in the nucleus thereby preventing expression of the nonlethal selectable phenotype by the nuclear genome and which comprises a translation initiation signal so placed as to be out of frame with respect to the DNA which encodes the nonlethal selectable phenotype.

This invention provides a method for obtaining a plant cell of a multicellular plant, the foreign DNA plastids of which cell have been transformed by a foreign DNA of interest, which comprises transforming the plastids of cells of the multicellular plant with the foreign DNA of interest and with DNA from which the translation initiation signal has been deleted and which encodes a nonlethal selectable phenotype expression of which phenotype by a cell occurs only when substantially all of the plastids of such cell have been transformed, and trans-splicing signals which cannot be processed in the nucleus thereby preventing expression of the selectable phenotype in the nuclear genome, selecting for cells which express the selectable phenotype, and thereby obtaining the plant cell, the plastids of which cell have been transformed by the foreign DNA of interest. In one example of this method, translation termination signals are inserted upstream of the DNA which encodes a nonlethal selectable phenotype and upstream of the trans splicing signals. In another example, the first exon of the Nicotania tabacum ribosomal protein gene rps12 is combined with the DNA from which the translation initiation signal has been deleted and which encodes a nonlethal selectable phenotype so that the translations initiation signal is correctly spliced to the DNA which encodes a nonlethal selectable phenotype in the plastid, but is not so spliced in the nucleus. In yet another example, the cell is stably transformed with DNA encoding the fused first and second exons of the rps12 gene such that trans-splicing by the plastid is unnecessary. The trans-splicing signals are plastid signals or heterologous signals.

This invention provides a method for obtaining a multicellular plant which has been transformed by a foreign DNA of interest which comprises stably transforming the plastids of the cells of the multicellular plant to insert DNA which encodes a nonlethal selectable phenotype and delete a gene in the absence of which the cells survive in culture but do not regenerate viable plants, selecting for cells which express such phenotype, inserting into the plastids of the resulting cells a microgenome which comprises DNA encoding the gene in the absence of which the cells survive in culture but do not regenerate viable plants and the foreign DNA of interest, and regenerating the multicellular plant which has been transformed by a foreign DNA of interest from the plant cells the plastids of which contain the microgenome. An example of a gene in the absence of which the cells survive in culture but do not regenerate viable plants is a photosynthetic gene and the selectable phenotype it encodes is green pigmentation.

This invention provides a method for obtaining a plant cell of a multicellular plant which has been transformed by a foreign DNA of interest, which comprises stably transforming the plastids of the cells of the multicellular plant to insert DNA which encodes a first nonlethal selectable phenotype and delete a gene in the absence of which the cells cannot survive in culture, and also inserting a microgenome which comprises DNA encoding the gene in the absence of which the cells cannot survive in culture and a second nonlethal selectable phenotype, selecting for cells which express the first phenotype, inserting into the plastids of the resulting cells a second microgenome which comprises DNA encoding a third nonlethal selectable phenotype and the foreign DNA of interest, selecting for cells which express the third phenotype and do not express the second phenotype, and thereby obtaining the plant cell which has been transformed by the foreign DNA of interest. Examples of nonlethal selectable phenotypes are certain antibiotic resistant phenotypes. An example of the gene in the absence of which the cells cannot survive in culture is a gene present in a single copy in the plastid genome, such as a tRNA gene.

This invention is useful to directly insert genes of choice into the plastid genome of a plant to create plants with particular desired characteristics. In addition, this invention is useful to elucidate the regulation of plastid gene expression, the interaction of plastid genes with nuclear genes, and the involvement of plastids in various biochemical and developmental processes to provide a sophisticated means for designing improved plants. For example, with information on the genetics of photosynthesis, the major solar energy transformation process, plants with improved photosynthetic capacity can be produced through stable plastid transformation. Therefore, applications of this invention will result in a better understanding of plastid functions and in improved crop plants.

This invention is illustrated in the Experimental Details section which follows. This section is set forth to aid in an understanding of the invention but are not intended to, and should not be construed to, limit in any way the invention as set forth in the claims which follow thereafter.

EXPERIMENTAL DETAILS

Example 1

This example demonstrates stable genetic transformation of the plastid genome in a higher plant, Nicotiana tabacum by selection for 16S rDNA encoded antibiotic resistance.

Materials and Methods

Plant lines: Two recipient lines were used. N. tabacum cv. Petit havana with its original cytoplasm, Nt (tbc), and the Nt (pbg) alloplasmic substitution line that has the nucleus of Nicotiana tabacum, and the cytoplasm of Nicotiana plumbagnifolia. The Nt(pbg) line is functionally male sterile because the filaments are shortened. Seeds, however, can be obtained by manual pollination. The Nt (pbg) line was obtained from Dr. Kevin Vaughn, USDA Delta States Research Center, Stoneville, Miss.

The *N. tabacum* SPC2 line has the original *N. tabacum* cytoplasm, and is a derivative of the SR1 mutant (Maliga, et el., 1973). SPC2 cells exhibit a high level of resistance to both streptomycin and spectinomycin. The two mutations are tightly linked (278 bp apart) and are due to a C860 to A (Etzold, et el., 1987), and a C1139 to U (Svab and Maliga, unpublished) change, respectively, in the 16S rDNA.

Transformation and regeneration of transgenic plants: For bombardment of leaf tissue, plants were aseptically grown from seed on MS medium. The MS medium is agar supplemented with MS salts (Murashige and Skoog, 1962) and sucrose (30 g/liter). Leaves were planted with abaxial side up on RMOP medium in a Petri dish. The RMOP medium consists of MS salts, $N^6$-benzyladenine (1 mg/liter), 1-napthaleneacetic acid (0.1 mg/liter), thiamine (1 mg/liter), inositol (100 mg/liter), agar (6 g/liter) at pH 5.8, and sucrose (30 g/liter).

Tungsten (1 μm) was prepared for transformation by mixing 25 μl of suspension (25 mg tungsten in 500 μl of $H_2O$) with 4 μg DNA dissolved in 5 μl $T_{10}E_1$ buffer (10 mM Tris, pH 8, 1 mM EDTA), 10 μl 2.5M $CaCl_2$ and 0.1M spermidine base. The particle—DNA mixture was incubated on ice for 2 min. and centrifuged for 1 min. in an Eppendorf centrifuge. After removing 25 μl of the supernatant, the tungsten was suspended by a brief (1 sec.) sonication, and applied to the macroprojectile (25 μl/bombardment). The bombardment was performed as described by Klein, et al., 1988.

Two days after bombardment the leaves were cut into sections (5 mm×5 mm) and transferred to RMOP medium containing 500 μg/ml of spectinomycin dihydrochloride. Green calli and shoots that formed on the bleached leaves were transferred onto the same selective medium. Shoots formed after a second selection on spectinomytin were rooted on MS medium to obtain plants. Cell culture procedures have been described in detail elsewhere (Maliga, 1984).

Leaf and seedling assays to test resistance phenotypes. Leaf sections of the regenerated plants were placed on a selective RMOP medium. Spectinomycin dihydrochloride (500 μg/ml) or streptomycin sulfate (500 ug/ml) will prevent greening of sensitive leaf callus on RMOP medium. Resistance phenotype of seedlings was determined by germinating surface-sterilized seeds on MS salts, 1% sucrose (Maliga, 1984). The antibiotics were filter sterilized, and added to the medium after autoclaving in the same concentration as for the leaf assay.

DNA manipulations: All DNA manipulations have been performed as described by Maniatis, et al. (Maniatis, et al., 1982). Cloning was carried out in the pBluescript I KS+ phagemid vector (Stratagene). Plastid DNA prepared according to Kolodner and Tewari, 1975. Designation and position of plastid genes is according to Shinozaki, et al., 1986. Total cellular DNA was prepared by the method of Fluhr, et al., 1984. DNA for Southern probing was labelled using a random primed DNA labeling kit (Boehringer Mannheim).

Results

Figure 1:
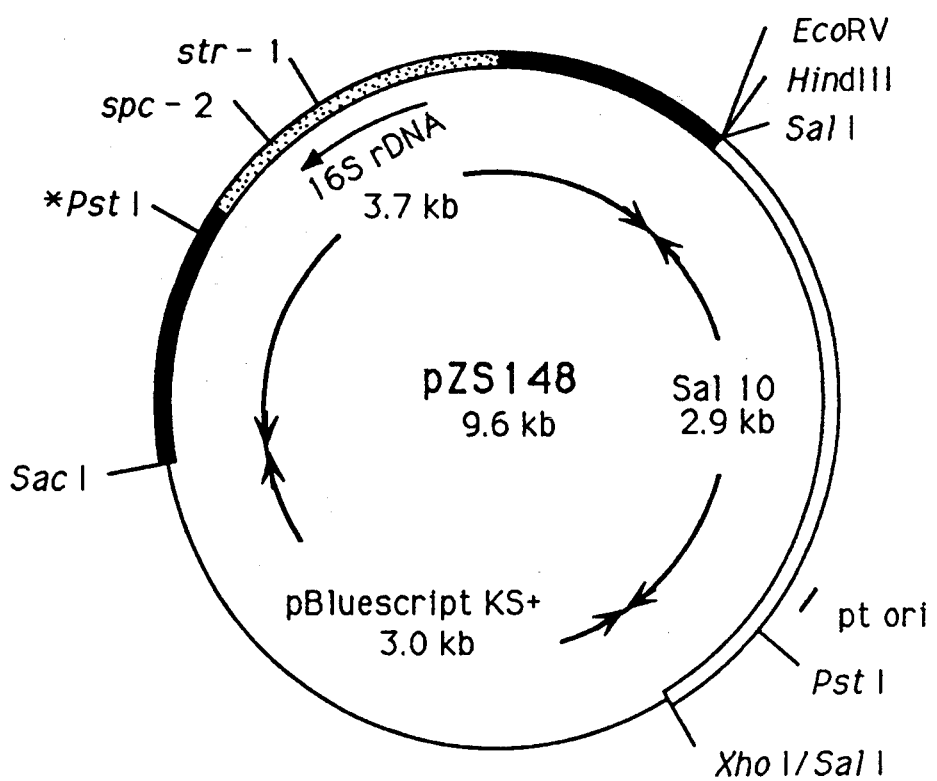
FIG. 1. The pZS148 plastid transformation vector.

Construction of the pZS148 plastid transformation vector: Plastid transformation vector pZS148 (FIG. 1) is derived from a pUC based plasmid (Vieira and Messing, 1982) and carries the 16S rRNA gene cloned as a 3.7 kb SacI-EcoRV fragment from the SPC2 ptDNA. The SPC2 line is resistant to streptomycin and to spectinomycin due to mutations in the 16S rRNA. An additional marker, a novel Pst I site, was generated 520 bp 3' to the spectinomycin resistance mutation, in the spacer region between the 16S rDNA and trnI genes, by inserting the synthetic oligonucleotide 5'-pd[GCTGCAGC]-3' into a StyI site. In addition, plasmid pZS148 carries the 2.9 kb SalI fragment, one of the regions implicated in ptDNA replication (Carillo and Bogorad, 1988). Plasmid pZS148 was deposited with the Patent Depository of the American Type Culture Collection (12301 Parklawn Drive, Rockville, Md. 20852) on Apr. 13, 1990, and designated the Accession Number ATCC40788. Plasmid pZS134 is identical to pZS148 except that it carries the 16S rDNA from the SR1 line that is sensitive to spectinomycin.

Spectinomycin resistant clones after transformation with pZS148 DNA: Whole leaves of Nt(tbc) and Nt(pbg) plants were bombarded with tungsten particles coated with pZS148 DNA according to the protocol of Klein et al., 1988a. In a sample of 148 bombarded leaves 56 spectinomycin resistant lines were obtained (Table 1). Different plants regenerated from the same resistant line are considered subclones and are designated by a capital letter. For example, plants Nt(pbg*)T2B and Nt(pbg*)T2D derive from the same clone, Nt(pbg*)T2.

In order to test the frequency of spontaneous spectinomycin resistant mutants, leaf tissue was bombarded with pZS134 DNA, and cultured on a drug containing medium, as described for the pZS148 DNA. In a sample of 50 bombarded leaves 6 spectinomycin resistant clones were recovered (Table 1). None of these clones were resistant to streptomycin (data not shown).

Spectinomycin resistance of the clones may be the result of transformation by the pZS148 DNA, or spontaneous mutation. The regenerated plants were therefore screened for the flanking unselected markers, the Pst I site and streptomycin resistance.

The unselected PstI marker in the spectinomycin resistant lines. The spectinomycin resistant clones were screened for the Pst I marker by Southern probing of total cellular DNA digested with Hind III and Pst I restriction endonucleases (FIG. 2A). In wild type Nt(tbc) or Nt(pbg) DNA the probe hybridizes to a 6.2 kb fragment. Replacement of the 16S rDNA region with the engineered SPC2 clone introduces a Pst I site into this 6.2 kb fragment, which results in the generation of a 4.4 kb and a 1.8 kb fragments. Based on the PstI marker three transplastgenic clones have been identified (Table 2).

TABLE 1

Selection of plastid transformants in leaf culture

| DNA | | No. of bombarded Leaves | No. of spectinomycin resistant clones | No. of Plastid transformants |
|---|---|---|---|---|
| pZS134 | Nt(pbg) | 39 | 5 | 0 |
| | Nt(tbc) | 11 | 1 | 0 |
| pZS148 | NT(pbg) | 58 | 26 | 2 |
| | NT(tbc) | 90 | 30 | 1 |

TABLE 2
Flanking markers in plastid transformants.

| Line | Subclone | Resistance to Sp500 | Resistance to Sm500 | PstI marker |
|---|---|---|---|---|
| Nt(pbg*)T2 | B | + | + | + |
|  | D | + | + | + |
| Nt(pbg*)T13 | A | + | − | + |
|  | B | + | − | + |
|  | C | + | − | + |
|  | M | + | + | + |
|  | P | + | + | + |
| Nt(tbc*)T85 | A | + | + | +/− |
|  | A1 | + | + | + |
|  | A2 | + | + | − |
|  | A3 | + | + | + |
|  | B | + | + | + |
|  | D | + | + | + |

Sp500 = 500 μg/ml spectinomycin dihydrochloride;
Sm500 = 500 μg/ml streptomycin sulfate Plants regenerated from the transplastgenic clones contained the Pst I marker (FIG. 2). In all but one, Nt(tbc*)T85A, there was no detectable amount of wild type fragment (FIG. 2). This indicates that the Pst I site was present in both rDNA repeats, and the wild-type fragment has been eliminated. In a leaf of one of the plants, Nt(tbc*)T85A, a mix of wild type and engineered 16SrDNA was found. Plants regenerated from the leaf of this plant carry a pure population of plastids with (85A1, 85A3) or without (85A2) the PstI marker. The plant without the Pst I marker is also resistant to both antibiotics (Table 2).

Plastid DNA was isolated from greenhouse grown plants approximately three months after the initial screen. PtDNA was probed as described above for total cellular DNA and was found to carry exclusively the Pst I marker (FIG. 2B). Inspection of ethidiumbromide stained Pst I ptDNA fragments also indicated the absence of 23.7 kb and 18.8 kb wild type Pst I fragments. Instead, novel 4.4 kb, 14.4 kb, and 19.3 kb fragments were found (FIG. 3).

Probing for the novel Pst I site in the 16S rDNA region is suitable to reveal a replicating pZS148 plasmid. If a replicating pZS148 plasmid is present hybridization to 4.5 kb, 2.7 kb and 2.4 kb fragments is expected (FIGS. 1,2) in addition to hybridization to the 4.4 kb and 1.8 kb fragments derived from the integrated 16S rDNA copy (FIGS. 2,3). Fragments characteristic of intact pZS148 plasmids were absent in all samples tested by Southern probing (FIG. 2) or in ethidium bromide stained gels (FIG. 3).

The unselected streptomycin resistance marker in the spectinomycin resistant lines: The spectinomycin resistant clones were also tested for the unselected antibiotic resistance marker, streptomycin resistance, in a leaf assay (FIG. 4). Plants regenerated from the Nt(pbg*)T2 and Nt(tbc*)T85 clones were phenotypically resistant to streptomycin. The Nt(pbg*)T13 line yielded both streptomycin resistant and sensitive plants (Table 2).

Inheritance of antibiotic resistance in the transplastgenic lines: Seeds were collected after selfing, and from reciprocal crosses with wild type N. tabacum. The seeds were germinated on selective media to test seed transmission of the transgenic traits (FIG. 5).

The seed progeny obtained after selfing is uniformly resistant to spectinomycin (Table 3). Lack of segregation indicates that the regenerated plants are homoplasmic for the spectinomycin resistance marker. They carry only one type, the spectinomycin resistant 16SrDNA. In crosses, the resistance is inherited maternally.

TABLE 3
Transmission of the Spectinomycin and Streptomycin Resistance to the Seed Progeny[a].

| | 0 | | | $Sp^{500}$ | | | $Sm^{500}$ | | | $Sm^{500}/Sp^{500}$ | | |
|---|---|---|---|---|---|---|---|---|---|---|---|---|
| | G | W | G/W | G | W | G/W | G | W | G/W | G | W | G/W |
| Nt(tbc) | 693 | 0 | 0 | 0 | 709 | 0 | 0 | 689 | 0 | 0 | 629 | 0 |
| Nt(tbc)SPC2 | 227 | 0 | 0 | 315 | 0 | 0 | 309 | 0 | 0 | 311 | 0 | 0 |
| Nt(pbg)T2C Self | 670 | 0 | 0 | 866 | 0 | 0 | 3 | 735 | 25 | 0 | 1090 | 16 |
| F1 | 774 | 0 | 0 | 1204 | 0 | 0 | 1 | 1405 | 20 | 0 | 1370 | 20 |
| RF1 | 355 | 0 | 0 | 0 | 413 | 0 | 0 | 522 | 0 | 0 | 517 | 0 |
| Nt(pbg)T2D Self | 294 | 0 | 0 | 653 | 0 | 0 | 173 | 511 | 62 | 208 | 557 | 40 |
| F1 | 522 | 0 | 0 | 447 | 0 | 0 | 297 | 369 | 100 | 283 | 329 | 78 |
| Rf1 | 421 | 0 | 0 | 0 | 553 | 0 | 0 | 609 | 0 | 0 | 719 | 0 |
| Nt(pbg)T13A Self | 832 | 0 | 0 | 967 | 0 | 0 | 1 | 1033 | 1 | 0 | 889 | 8 |
| F1 | 998 | 0 | 0 | 840 | 0 | 0 | 2 | 1112 | 11 | 1 | 659 | 12 |
| RF1 | 650 | 0 | 0 | 0 | 1053 | 0 | 0 | 1030 | 0 | 0 | 1034 | 0 |
| Nt(pbg)T13C Self | 580 | 0 | 0 | 766 | 0 | 0 | 4 | 703 | 8 | 4 | 871 | 9 |
| F1 | 1194 | 0 | 0 | 1203 | 0 | 0 | 0 | 1342 | 7 | 0 | 980 | 3 |
| RF1 | 495 | 0 | 0 | 0 | 467 | 0 | 0 | 602 | 2 | 00 | 60 | 4 |
| Nt(tbc)T85A Self | 497 | 0 | 0 | 556 | 0 | 0 | 0 | 524 | 0 | 0 | 423 | 0 |
| F1 | 352 | 0 | 0 | 546 | 0 | 0 | 0 | 412 | 0 | 1 | 420 | 3 |
| FR1 | 531 | 0 | 0 | 0 | 614 | 0 | 0 | 614 | 0 | 0 | 656 | 0 |
| Nt(tbc)T85B Self | 592 | 0 | 0 | 635 | 0 | 0 | 179 | 437 | 65 | 274 | 291 | 81 |
| F1 | 504 | 0 | 0 | 456 | 0 | 0 | 390 | 136 | 31 | 293 | 90 | 30 |
| RF1 | 810 | 0 | 0 | 0 | 907 | (2)[b] | 0 | 861 | 0 | 0 | 950 | 0 |

The unselected streptomycin resistance was also maternally inherited. Segregation for this trait, however, was found in the selfed seed progeny, and in F1, in the three lines. In addition to the resistant (green) and sensitive (white) seedlings, variegated plants were also observed (FIG. 5). Variegation for the streptomycin resistance marker in the progeny indicates that the regenerated plants were heteroplasmic for the unselected streptomycin resistance trait.

The ratio of resistant to variegated to sensitive seedlings differs in subclones of the same line (compare e.g. the Nt(pbg*)T2D and Nt(pbg*)T2C progenies in Table 3). Note that streptomycin resistant seedlings were found in the seed progeny of the Nt(pbg*)T13A and 13C plants although the plants were phenotypically sensitive in the leaf assay (Table 2). Furthermore, the Nt(tbc*)T85A plant was phenotypically resistant to streptomycin in the leaf assay (Table 2) but was segregating streptomycin resistant seed progeny. These inconsistencies are due to chimerism in the plants, resulting from random sorting of plastids in the absence of selection.

Discussion

The conclusion that spectinomycin resistance in three of the lines is due to transformation is based on recovering the two linked, unselected traits in the same clones. The 148 bombarded samples yielded 3 transplastgenic clones, that is one clone per 50 bombardments (Table 1). Selection for nuclear antibiotic resistance markers yields two to six transgenic clones per bombardment following the same protocol (Klein et al., 1988b). Accordingly, transformation of plastids in our hands is about 100 fold less efficient than transformation of the nucleus despite the high number of ptDNA copies in a cell (see below). This contrasts with the Chlamydomonas system (Boynton, et al. 1988; Blowers, et al. 1989) in which plastid transformation is at least as efficient as nuclear gene transformation (Kindle et al., 1989) yielding 2 to 100 transplastgenic clones per bombardment.

Transgenic plastids have been obtained by selection for the non-lethal marker spectinomycin resistance. We consider non-lethal selection critical in obtaining the transplastgenic lines. Higher plants carry a large number of identical plastid genome copies per cell. In N. tabacum the 3,000 to 12,000 copies (Cannon et al., 1985; Yasuda et al., 1988) are localized in up to a hundred plastids (Thomas and Rose, 1983). This contrasts with the 80 ptDNA copies, carried by a single plastid in Chlamydomonas (Harris, 1989). Non-lethal selection in higher plants allows sufficient time for the resistant plastid genome copies to increase in numbers to allow phenotypic expression.

Plastid transformation is rare, therefore we assume that in a transplastgenic clone all plastids derive from the same transformed organelle. In each clone more than one type of transgenic plastid genome was found. Our findings can be explained by assuming a multi-step process, involving DNA recombination, copy correction, and sorting out of the transgenic ptDNA copies. Different transgenic plastid genomes may be products of the same initial transformation event, or independent recombination events between copies of vector pZS148 and different copies of ptDNA. The initial transformation event is then followed by copy correction, a mechanism that maintains identical DNA sequence in the two repeat regions of ptDNA (Shinozaki et al., 1986). Copy correction may also generate different transgenic plastid genomes using different copies of the same template. Subsequently, sorting of ptDNA should yield homoplasmic organelles, then homoplasmic cells.

Example 2

This example demonstrates stable genetic transformation of the plastid genome by selection for chimeric antibiotic resistance genes that contain plastid introns and trans-splicing signals.

Non-lethal selection is carried out by chimeric (i.e. nonplastid) genes expressed under the control of plastid expression signals. These genes encode enzymes that inactivate streptomycin or spectinomycin by phosphorylation or adenylation, therefore resistant cells expressing the genes can be identified by their green color, similarly to resistant lines transformed with the antibiotic resistant 16S rDNA clones. (Genes suitable to inactivate streptomycin or spectinomycin are described in Maliga et al., 1988; and Svab et al. 1990). Plastid gene promoters, however, have been shown to function in the nucleus, and the genes used for selection markers are not plastid genes, as was the case in example 1. Since frequency of nuclear gene transformation is much higher than that of plastid transformation use of such genes is not practical, unless nuclear gene expression can be prevented or reduced. A chimeric plastid gene construct which is not expressed properly in the nucleus will not yield resistant clones if inserted into nuclear DNA. Such gene constructs are obtained by incorporation of plastid introns, and of plastid trans-splicing signals, in the chimeric genes. Examples of such chimeric gene constructs are described below.

In one example, a cistron which includes the AUG codon and the other sequences which form a favorable context for translation initiation in the cytoplasm (described in Kozak, 1989) and a translation termination sequence, is incorporated within an intron in the leader sequence of the chimeric selectable marker gene, which also carries the foreign DNA insert. The small subunit of eukaryotic ribosomes is believed to bind initially at the capped 5'-end of messenger RNA and then migrate, stopping at the first AUG codon it reaches that is in a favorable context for initiating translation. If a second cistron is inserted upstream of a gene, expression of the downstream cistron (here, the selectable marker gene) is drastically reduced (500 to 1,500 fold) as shown by Angenon et al., 1989. Using the method of example 1, cells are stably transformed to homoplasmy with this DNA construct. The plastid intron containing the AUG codon and the translation termination sequence cannot be deleted by the nuclear splicing mechanism, therefore the mRNA produced in the nucleus contains both AUG codons with a translation termination sequence between them, which reduces expression as described because termination occurs after the first AUG codon. Reduced expression of a selectable marker prevents expression of the phenotype, consequently the nuclear transformants are not identified. The upstream cistron, however, is incorporated into a plastid intron. When the same gene is introduced into the plastids, the upstream cistron is removed with the intron, and resistance is expressed from the downstream cistron, which comprises the selectable marker gene. If the selectable marker is an antibiotic resistance gene as described supra, then the translation product of the correctly spliced mRNA is the functional antibiotic modifying enzyme allowing expression of the non-lethal antibiotic resistance phenotype. Introns in Nicotiana tabacum ptDNA have been reviewed by Sugiura, 1987. Some of the conserved plastid intron-exon junction sequences resemble the conserved Junction sequences of nuclear gene introns, others do not. The latter class of plastid introns is suitable to prevent correct expression of plastid marker genes in the nucleus.

In another example, the plastid intron contains out of frame translation initiation signals in a favorable context (Kozak, 1989) so that translation in the cytoplasm is initiated in the region of the mRNA encoded by the intron. Using the method of example 1, cells are stably transformed to homoplasty with the DNA construct containing the intron, the selectable marker gene, and the insert gene. In the plastid, the intron is deleted and the mRNA produced has only the correctly located translation initiation signal for the selectable marker gene. However, in the nucleus, the plastid intron is not spliced out and the mRNA produced contains an out of frame translation initiation signal. As discussed supra, the eukaryotic ribosome binds to the first such signal it finds. The translation products of this mRNA in the cytoplasm are enzymatically inactive fusion proteins. If the selectable marker is an antibiotic resistance gene as described supra, then the translation product of the correctly spliced mRNA is the functional antibiotic modifying enzyme allowing expression of the non-lethal antibiotic resistance phenotype.

In yet another example, an intron is incorporated in the 5' end of the coding region of the chimetic selectable marker gene, and contains one or more stop codons (translation termination signals). Using the method of example 1, cells are stably transformed to homoplasmy with the DNA construct containing the intron, the selectable marker gene, and the insert gene. The plastid intron splicing signals are not recognized in the nucleus, therefore the introns will not be removed and the cytoplasmic mRNA will contain the stop codons. Translation initiated in the cytoplasm at the proper AUG therefore will be terminated prematurely (incorporation of translation termination signals in the intron will result in dissociation of the cytoplasmic ribosomes in the region of mRNA encoded by the intron). The plastid intron, however, is removed from the mRNA when the chimeric gene is integrated into the plastid, therefore translation will be terminated at the proper stop codon. If the selectable marker gene is an antibiotic resistance gene as described supra, then the translation product of the correctly spliced mRNA is the functional antibiotic modifying enzyme allowing expression of the non-lethal antibiotic resistance phenotype.

Another means of preventing nuclear expression of the nonlethal selectable marker is incorporation of trans-splicing signals in the 5' end of the chimeric selectable marker gene. Trans-splicing is a mechanism by which functional mRNA is created from independent plastid transcripts. (Sugiura, 1987). Trans-splicing is also suitable to achieve selective expression of chimetic genes in plastids. The nuclear splicing mechanisms cannot interpret plastid trans-splicing signals correctly. Therefore if the construct is arranged so that it is necessary to trans-splice in order to place the translation initiation signal in the correct location relative to the selectable marker gene for expression to occur, this will happen in the plastid but not in the nucleus, so that the selectable marker will only be expressed by the plastid genome. The 5' end of the coding region, including the translation initiation codon, is removed. Using the method of example 1, cells are stably transformed to homoplasmy with the DNA construct containing transsplicing signals, the 5' deleted selectable marker gene, and the insert DNA. When the gene is transcribed in the nucleus, the mRNA is not translated in the cytoplasm in the absence of an AUG initiation codon. A translatable message, however, is assembled in the plastids by trans splicing. If the selectable marker gene is an antibiotic resistance gene as described supra, then the translation product of the correctly spliced mRNA is the functional antibiotic modifying enzyme allowing expression of the non-lethal antibiotic resistance phenotype.

In one example of a suitable DNA construct for this purpose, the first exon of the *N. tabacum* ribosomal protein gene rps12 is combined with the truncated selectable marker gene which also carries the insert DNA. Trans-splicing results in two products in transgenic plastids. The normal rps12 mRNA, and a chimeric mRNA composed of the first exon of rpS12 encoding 38 amino acids of rpS12 and the enzyme conferring the antibiotic resistance phenotype. However, the nucleus cannot trans-splice so that the mRNA produced is not correctly arranged for translation. Trans-splicing of the rps12 gene is described in Torazawa et al., 1986. In an advanced example of the procedure, the coding region of exon 1 and exon 2 of the rps12 gene are fused in vitro, and introduced into the ptDNA by replacing exon 2 with the fused segment by stably transforming the plastids of the recipient cell by the method of example I so that all the plastids have the fused segment. The wild-type arrangement is such that exon 1 of the rps12 gene is at a distance from exons 2 and 3, so ordinarily rps12 is translated from a transcript that has been trans spliced together from 2 messages, one encoding the translation initiation signal (start signal) and exon 1, the other encoding exons 2 and 3. If trans-splicing does not occur, exons 2 and 3 will not be translated because they lack start signals. But in the transformed plastid genomes, exon 1 with its start signal has been placed next to exons 2 and 3, so that trans splicing is not necessary because all the exons can be encoded by one message. This arrangement eliminates the need for trans-splicing of the rps12 gene. In a cell that carries the fused rps12 gene in its ptDNA the trans-splicing signals are available for the exclusive assembly of chimeric antibiotic resistance genes, and thereby this line serves as a specific recipient strain for plastid transformation. In this recipient the N-terminus of a suitable chimeric selectable marker gene, such as a gene encoding spectinomycin resistance, is combined with the exon 1 trans-splicing signals. This cell is an efficient recipient for transformation with the C-terminus of the selectable marker gene that carries the rps12 exon 2 trans-splicing signals. Upon plastid transformation the rps12 trans-splicing system creates a functional message in plastids, thereby facilitating recovery of plastid transformants. Accordingly, the C-terminus of the coding region of a selectable marker gene, supplied with plastid gene expression signals, translation initiation and/or termination signals, and the rps12 trans-splicing signals is combined with a gene of interest. The C-terminus of the selectable marker gene is not expressed in the nucleus, as discussed above, therefore plastid transformants are efficiently selected using this split marker system. The gene of interest is introduced by cotransformation, linked to the C-terminus of the selectable gene. Other arrangements utilize trans-splicing signals from heterologous species, such as Chlamydomonas plastids (Choquet et al., 1988), or artificial trans-splicing sequences that provide new specificity.

Transformation, and selection of transplastgenic clones is carried out as described in Example 1. Cotransformation with these markers is suitable to introduce unselected, desirable genes. Integration of the selectable marker genes, and of the linked, non-selectable genes that encode desirable characteristics is directed by ligating them into intergenic regions in cloned ptDNA fragments. Selection for the marker gene results in the insertion of the marker, and of the linked unselected gene, into the plastid genome by homologous recombination of the plastid intergenic regions in the DNA construct with homologous regions in the plastid. Insertion of this type is described in Blowers et al., 1989. An example of a site suitable for integration without disrupting vital plastid functions is the StyI site 3' to the 16S rDNA into which a synthetic oligonucleotide was inserted in Example I. Other suitable sites in *N. tabacum* are selected based on the plastid DNA sequence of Shinozaki et al., 1986.

Genes of interest are also introduced into the plastid genome when carried by a separate plasmid. An example of cotransformation using two marker genes on separate plasmids is given by Schocher et al., 1986. The gene of interest must be cloned into an intergenic region of the plastid DNA so that the insertion of the gene into the plasmid genome will not result in disruption of any vital plasmid functions.

Example 3

This example demonstrates stable genetic transformation of plastids using a binary plastid transformation vector.

Stable transformation of plastids by gene replacement is rare in higher plants, as discussed in Example 1. For gene replacement to occur two homologous recombination events are required. That is one reason why stable integration of transforming DNA is rare (about 1%) relative to the frequency of successful DNA introductions, as shown in Klein et al., 1988b. Introduction of the gene of interest on an autonomously replicating vector eliminates the requirement for integration, and thereby increases plastid transformation frequency. This is achieved by the plastid binary vector system designed after the Agrobacterium binary transformation vector system described in Hoekema et al., 1983; and Weising et. al., 1988. The binary plastid vector system comprises two complementing, independently replicating circular DNA molecules, the macrogenome and the microgenome.

The macrogenome is the native plastid genome with a small portion of the genome deleted, therefore the plastids that carry a pure population of macrogenomes do not support plant growth under field conditions. The deletion is essential so that no plastid is maintained without a microgenome that carries the gene of interest, thereby providing the stability of the binary system. The plastids of the cell are transformed to delete the gene that is carried by the microgenome so that the microgenome is therefore required to complement the deletion. The deleted plastid genomes are referred to as macrogenomes. The deleted gene that secures the maintenance of the microgenome is the stabilizer gene. If the stabilizer gene is a gene not vital for survival in culture, such as a photosynthetic gene, the cells that carry a pure population of macrogenomes will survive in culture since sucrose in the culture dispenses with the requirement for photosynthesis. If the stabilizer gene is a housekeeping gene, such as a tRNA gene that is present only in a single copy in the plastid genome, cells that carry a pure population of macrogenomes will not survive in culture since plastid protein synthesis is required for the maintenance of the organelle compartment. In these cells the complementing microgenome should be present in the plastids at all times. The macrogenome is complemented with the microgenome carrying the deleted portion, or the deleted portion and additional genes of interest.

The microgenome carries a copy of the stabilizer gene, and DNA sequences that facilitate its replication in plastids. The stabilizer gene may be the gene of interest, such as the psbA gene that confers herbicide resistant. In addition, the microgenome may carry a selectable marker gene, if the gene of interest does not have a selectable phenotype. The microgenome carries two replication origins, one that allows its replication in *E. coli*, and one that supports its replication in plastids. Genes carried by the microgenome are conveniently modified in *E. coli* and subsequently introduced into the plastids of higher plants. The replication origin may derive from homologous sources, such as those cited in Daniell et al., 1990. The replication origin may also derive from a heterologous source such as Euglena gracillis plastids (Ravel-Chapuis et al., 1982), or a geminivirus such as abutilon mosaic virus (Groning et al., 1990). Application of the plastid binary system is described below according to the type of stabilizer gene used.

The stabilizer gene is dispensable in culture. Plant cells are viable in culture if they carry only macrogenomes since photosynthesis is not required in a sucrose-containing medium (However, these cells cannot regenerate viable plants because, unlike cells in culture, plants in the field must be able to perform photosynthesis to survive). The microgenomes are manipulated in *E. coli*, and introduced into the plastids as described in Example 1. Cells with deletions of photosynthesis genes are typically non-pigmented. Transformation restores photosynthetic ability, and greening, a color that allows easy identification of transplastgenic lines. If deletion of the photosynthetic gene does not result in the loss of pigmentation, the antibiotic resistance gene included on the microgenome is used to select the transplastgenic lines.

The deleted gene is a housekeeping gene: If the deleted gene is a non-photosynthetic gene that is required for the maintenance of organelle continuity, a complementing microgenome should be present at all times. In this case two different microgenomes are used, carrying different antibiotic resistance markers. In one example, the microgenome carried by the plastids (Microgenome I) contains a streptomycin resistance gene, such as a gene encoding a streptomycin phosphotransferase enzyme engineered for expression in plastids. The microgenome that is to be introduced carries a spectinomycin resistance gene (Microgenome 2), such as a gene encoding the amino-glycoside adenyltransferase enzyme. Following the introduction of the plastid transformation vector the cells are selected for spectinomycin resistance. Since one microgenome is sufficient to maintain the organelle continuity the original microgenomes are lost. This manipulation results in an efficient exchange of Microgenome I for Microgenome II, the frequency of exchange being dependent only on the efficiency of introducing Microgenome II into the plastids.

An example of this procedure using a photosynthetic stabilizer gene nonvital in culture follows: First, the cells are transformed to convert the plastid population into macrogenomes, i.e., the stabilizer gene is deleted from all the plastids in the cell. This is accomplished by homologous recombination. The stabilizer gene, b, is flanked in the plastid genome by the genes a and c. A DNA construct is made which consists of a selectable marker gene flanked by the genes a and c. The cell is then transformed with this DNA using the transformation system described in Example 1. Selection yields cells that are homoplasmic for plastids that have integrated the construct by homologous recombination and have thereby replaced gene b with the selectable marker gene. The plastid genomes are now macrogenomes. The cells can survive in culture without gene b, but they cannot be regenerated into plants without gene b. The cells are transformed with the microgenome, which contains gene b and the foreign gene with which the cell is to be transformed (alternatively, an improved version of gene b may be the gene inserted). Only those cells which maintain the microgenome bearing the foreign gene can be developed into viable plants.

An example of this procedure using a housekeeping gene for a unique tRNA without which the cell cannot survive follows: As in the example above, the cells must first be transformed to delete the housekeeping gene b from the plastid population. However, the cells cannot survive without gene b, so the microgenome must be inserted at the same time.

The DNA construct used to transform the plastid population by the method of Example 1 contains antibiotic resistance gene 1. The microgenome contains antibiotic resistance gene 2. Selection for antibiotic i yields cells homoplasmic for the deleted plastid (macrogenome) and containing the microgenome with gene b that was deleted from the macrogenomes. To insert the foreign gene of choice, it is easy to exchange the microgenome already in the cells for a second microgenome containing the foreign gene. The second microgenome contains antibiotic resistance gene 3. The cells are transformed with this microgenome, and cells resistant to antibiotic 3 but sensitive to antibiotic 2, i.e. cells which have replaced the first microgenome with the second microgenome, are easily selected. Any microgenome bearing a foreign gene can be conveniently inserted using the microgenome replacement method.

REFERENCES

Angenon G, Uotila S, Kurkela S A, Teeri T M, Botterman J, Van Montagu M (1989) Expression of dicistronic transcriptionalunits in transgenic tobacco. Molecular and Cellular Biology 9: 5676–5684, 1989.

Benfey P N, Chua N H (1989) Regulated genes in transgenic plants. Science 244: 174–181.

Blowers A D, Bogorad L, Shark K B, Sanford J C (1989) Studies on Chlamydomonas chloroplast transformation: Foreign DNA can be stably maintained in the chromosome. The Plant Cell 1: 123–132.

Boyer C T, Shannon J C, Hardison R C (eds.) Physiology, Biochemistry, and Genetics of Nongreen Plastids. (Amer. Soc. Plant Physiol., Rockville, Md. 1989)

Boynton J E, Gillham N W, Harris E H, Hosler J P, Johnson A M, Jones A R, Randolph-Anderson B L, Robertson D, Klein T M, Shark K B, Sanford J C (1988) Chloroplast transformation in Chlamydomonas with high velocity microprojectiles. Science 240: 1534–1538.

Boynton J E, Gillham N W, Harris E H, Newman S M, Randolph-Anderson B L, Johnson A M, Jones A R (1990) Manipulating the chloroplast genome of Chlamydomonas; Molecular genetics and transformation. M. Baltscheffsky (ed.), Current Research in Photosynthesis, Vol. III, Kluwer Academic Publishers, Amsterdam, pp. 509–516 in press.

Cannon G, Heinhorst S, Siedlecki J, Weissbach A (1985) Chloroplast DNA synthesis in light and dark grown cultured *Nicotiana tabacum* cells as determined by molecular hybridization. Plant Cell Reports 4: 41–45.

Carillo N, Bogorad L (1988) Chloroplast DNA replication in vitro: site-specific initiation from preferred templates. Nucleic Acids Research 16: 5603–5620.

Choquet Y, Goldschmidt-Clermont M, Girard-Bascon J, Kuck U, Bennoun P, Rochaix J D (1988) Mutant phenotypes support a trans-splicing mechanism for the expression of the tripartite psaA gene in the C. reinhardtii chloroplast. Cell 52: 903–913.

Comai L, Faciotta D, Hiatt W R, Thompson G, Rose E R, Stalker D M (1985) Expression in plants of a mutant aroA gene from Salmonella typhimurium confers tolerance to glyphosate. Nature 317: 741–744.

Cornelissen M and Vandewiele M (1989) Nuclear transcriptional activity of the tobacco plastid psbA promoter. Nucleic Acids Research 17: 19–28.

Cseplo A, Medgyesy P, Hideg E, Demeter S, Marton L, Maliga P. (1985) Triazine resistant Nicotiana mutants from photomixotrophic cell cultures. Mol. Gen. Genet. 200: 508–510.

Cseplo A, Etzold T, Schell J, Schreier P (1988) Point mutations in the 23S rRNA genes of four lincomycin resistant Nicotiana plumbaginifolia mutants could provide new selectable markers for chloroplast transformation. Mol. Gen. Genet. 214: 295–299.

Cseplo A and Maliga P (1984) Large scale isolation of maternally inherited lincomycin resistance mutations in Nicotiana plumbaginifolia. Mol. Gen. Genet. 196: 407–412.

Daniel H, McFadden B A (1987) Uptake and expression of bacterial and cyanobacterial genes by isolated cucumber etioplasts. Proc. Natl. Acad. Sci. USA 84: 6349–6353.

Daniell H, Vivekananda J, Nielson B L, Ye G N, Tewari K K, Sanford J C (1990) Transient foreign gene expression in chloroplasts of cultured tobacco cells after biolistic delivery of chloroplast vectors. Proc Natl Acad Sci U.S.A 87: 88–92.

deBlock M, Schell, J, Van Montagu M (1985) Chloroplast transformation by Agrobacterium tumefaciens. EMBO J 4: 1367–1372.

Durbin R D, Uchytil T F (1977) Cytoplasmic inheritance of chloroplast coupling factor 1. Biochem. Genetics 15: 1143–1145.

Erickson J E, Rhehire M, Rochaix J D, Mets L. (1985) Herbicide resistance and cross-resistance: changes at three distinct sites in the herbicide-binding protein. Science 228: 204–207.

Etzold T, Fritz C C, Schell J, Schreier P H (1987) A point mutation in the chloroplast 16S rRNA gene of a streptomycin resistant *Nicotiana tabacum*. FEBS Lett 219: 343–346

Fejes E, Engler D, Maliga P (1990) Extensive homologous chloroplast DNA recombination in the pt14 Nicotiana somatic hybrid. Theor. Appl. Genet. 79: 28–32.

Fluhr R, Aviv D, Galun E, Edelman M (1984) Generation of heteroplastidic Nicotiana cybrids by protoplast fusion: analysis for plastid recombinant types. Theor Appl Genet 67: 491–497.

Fromm H, Galun E, Edelman M (1989) A novel site for streptomycin resistance in the '530 loop' of chloroplast 16S ribosomal RNA. Plant Molecular Biology 12: 499–505

Fromm H, Edelman M, Aviv D, Galun E (1987) The molecular basis for rDNA dependent spectinomycin resistance in Nicotiana chloroplasts. EMBO J 6: 3233–3237

Fromm M E, Taylor L P, Walbot V (1986) Stable transformation of maize after gene transfer by electroporation. Nature 319: 791–793.

Groning B R, Frischmonth I. Jeske H. (1990) Replicative form DNA of abuliton mosaic virus is present in plastids. Mol. Gen. Genet. 220: 485–488.

Gruissem W (1989) Chloroplast gene expression: How plants turn their plastids on. Cell 56: 161–170.

Harris EH (1989) The Chlamydomonas Sourcebook. (Academic Press, San Diego), p. 354.

Harris E H, Burkhart B D, Gillham N W, Boynton J E (1989) Antibiotic resistance mutations in the chloroplast 16S and 23S rRNA genes of Chlamydomonas reinhardtii: Correlation of genetic and physical maps of the chloroplast genome. Genetics 123: 281–292.

Haughn G W, et al. Smith J. Mazur B. Somerville C. (1988) Transformation with a mutant Arabidopsis acetolacetate synthase gene renders tobacco resistant to sulfonylurea herbicides. Mol. Gen. Genet. 211: 266–271.

Hoekema A, Hirsch P R, Hooykaas P J J, Schilperoort R A (1983) A binary plant vector based on separation of vir—and T-region of the Agrobacterium tumefaciens Ti-plasmid. Nature 303: 179–180.

Kindle, K L, Schnell R A, Fernandez E, Lefebvre P A, Stable nuclear transformation of Chlamydomonas using the Chlamydomonas gene for nitrate reductase. (1989), J. Cell Biol. 109: 2589–2601.

Klein T M, Gradziel T, Fromm M E, Sanford J C (1988a) Factors influencing gene delivery into Zea mays cells by high velocity microprojectiles. Bio/Technology 6: 559–563.

Klein T M, Harper E C, Svab Z, Sanford J C, Fromm M E, Maliga P (1988b) Stable genetic transformation of intact Nicotiana cells by the particle bombardment process. Proc Natl. Acad. Sci. USA 85: 8502–8505.

Kolodner R, Tewari K K (1975) The molecular size and conformation of the chloroplast DNA from higher plants. Biochim. Biophys. Acta 402: 372–390.

Kozak (1989) The scanning model for translation, an update. J. Cell Biol. 108: 229–241.

Krens F A, Molendijk L, Wullems G J, Schilperoort R A (1982) In vitro transformation of plant protoplast with Ti-plasmid DNA. Nature 296: 72–74.

Lee K Y, Townsend J, Tepperman S, Black M, Chui C F, Mazur B, Dunsmuir P, Bedbrook S. (1988) The molecular basis of sulfonylurea resistance in tobacco. EMBO J. 7: 1241–1248.

Maliga P (1984) Cell Culture procedures in mutant selection and characterization in Nicotiana plumbaginifolia. In: Vasil IK (ed) Cell culture and somatic cell genetics of plants. Vol 1. Academic Press, Orlando, pp 552–526

Maliga P, Breznovits A, Marton L (1973) Streptomycin resistant plants from callus culture of haploid tobacco. Nature 255: 401–402.

Maliga P, Moll B, Svab Z (1990) Toward manipulation of plastid genes in higher plants. In: Zelitch I (ed) Perspectives in genetic and biochemical regulation of photosynthesis, Alan R. Liss, New York, pp 133–143

Maliga P, Svab Z, Harper C, Jones J D G (1988) Improved expression of streptomycin resistance in plants due to a deletion in the streptomycin phosphotransferase coding sequence. Mol. Gen. Genet. 214: 456–459.

Maniatis T, Fritsch E F, Sambrook J (1982) Molecular cloning: a laboratory manual. Cold Spring Habor Laboratory, Cold Spring Harbor, N.Y.

Medgyesy P, Fejes E, Maliga P (1985) Interspecific chloroplast recombination in a Nicotiana somatic hybrid. Proc. Natl. Acad Sci. 82: 6960–6964.

Murashige T, Skoog F (1962) A revised medium for the growth and bioassay with tobacco tissue culture. Physiol Plant 15: 473–497.

Negrutia I, Shillito R, Potrykus I, Biasini G, Sala F. (1987) Hybrid genes in the analysis of transformation conditions. Plant Molec. Biol. 8: 363–373.

Palmer J D (1985) Comparative organization of chloroplast genomes. Ann Rev Genet 19: 325–354

Pay A, Smith M A, Nagy F, Marton L (1988) Sequence of the psbA gene from wild-type and triazine resistant Nicotiana plumbaginifolia. Nucleic Acids Res. 16: 8176.

Possingham J V, Lawrence M E (1983) Controls to plastid division. Int Rev Cytol 84: 1–56

Ravel-Chapuis P, Heizmann P, Nigon V (1982) Electron microscopic localization of the replication origin of Euglena gracillis chloroplast DNA. Nature 300: 78–81.

Sato F, Shigematsu Y, Yamada Y (1988) Selection of an atrazine-resistant tobacco cell line having a mutant psbA gene. Mol. Gen. Genet. 214: 358–360.

Schocher R J, Shillito R D, Saul M W, Paskowski J, Potrykus I (1986) Co-transformation of unlinked foreign genes into plants by direct gene transfer. Biotechnology 4: 1093–1096.

Shah D M, Horsch R B, Klee H J, Kishore G M, Winter J A, Tumer N E, Hiranoka, C M, Sanders P R, Gasser C S, Aykent S, Siegel N R, Rogers S G, Fraley R T. (1986) Engineering herbicide tolerance in transgenic plants. Science 233: 478–481.

Shinozaki K, Ohma M, Tanaka M, Wakasugi T, Hayashida N, Matsubyashi T, Zaita N, Chunwongse J, Obokata J, Yamaguchi-Shinozaki K, Ohto C, Torazawa K, Mong B Y, Sugita M, Deno H, Kamogashira T, Yamada K, Kusuda J, Takaiwa F, Kato A, Tohdoh N, Shimada H, Sugiura M (1986) The complete nucleotide sequence of the tobacco chloroplast genome; its organization and expression. EMBO J 5: 2043–2049.

Sugiura M. (1987) Structure and function of the tobacco chloroplast genome. Bot. Mag. Tokyo 100: 407–436.

Svab Z, Harper E C, Jones J D G, Maliga P (1990) Aminoglycoside 3"-adenyltransferase confers resistance to spectinomycin in Nicotania tabacum. Plant Molecular Biology 14: 197–205.

Thanh N D, Medgyesy P (1989) Limited chloroplast gene transfer via recombination overcomes plastome-genome incompatibility between Nicotiana tabacum and Solanum tuberosum. Plant Mol. Biol. 12: 87–93.

Thomas M R, Rose R J (1983) Plastid number and plastid structural changes associated with tobacco mesophyll protoplast cultures and plant regeneration. Planta 158: 329–338.

Torazawa K, Hayashida N, Obakata J, Shinozaki K, Sugiura M (1986) THe 5' part of the gene for ribosomal protein S12 is located 30 kbp donwnstream from its 3' part in the tobacco chloroplast genome. Nucleic Acid research 14: 3143.

Vancanneyt G, Schmidt R, O'Connor-Sanchez A, Willmitzer L, Roche-Sose M. (1990) Construction of an intron-containing marker gene: splicing of the intron in transgenic plants and its use in monitoring early events in Agrobacterium-mediated plant transformation. Mol. Gen. Genet. 220: 245–250.

Vieira, J. and Messing, J. (1982) Production of single-stranded plasmid DNA. Gene 19: 259–268.

Weising K, Schell J, Kahl G (1988) Foreign genes in plants: transfer structure, expression and applications. Annu Rev Genet 22:421–477.

Yasuda T, Kuroiwa T, Nagata T (1988) Preferential synthesis of plastid DNA and increased replication of plastids in cultured tobacco cells following medium renewal. Planta 174: 235–241.

Zurawski G, Clegg M T (1987) Evolution of higher-plant chloroplast DNA-encoded genes: implication for structure-function and phylogenetic studies. Ann. Rev. Plant Physiol. 38: 391–418.

What is claimed is:

1. A method for obtaining stably plastid-transformed cells of a multicellular plant, which comprises:
   a) transforming plastids of said cells with a DNA molecule having:
      i) a targeting segment comprising a DNA sequence substantially homologous to a pre-determined sequence of a plastid genome, said targeting segment enabling insertion of said DNA molecule into said plastid genome by homologous recombination with said pre-determined sequence;
      ii) a selectable marker sequence disposed within said targeting segment, said selectable marker sequence being selected from the group consisting of: a sequence encoding a form of plastid 16S ribosomal that is resistant to spectinomycin or streptomycin, and a sequence encoding a heterologous protein that inactivates spectinomycin or streptomycin, said selectable marker sequence conferring a selectable phenotype to cells having substantially all plastids transformed with said DNA molecule; and
      iii) at least one cloning site adapted for insertion of at least one additional DNA segment, said at least one cloning site being disposed within said targeting segment relative to said selectable marker sequence so as not to interfere with said conferring of said selectable phenotype;
   b) maintaining said cells in a selection medium which permits survival of cells having transformed or non-transformed plastids, and which further permits expression of said selectable phenotype in cells having substantially all plastids transformed with said DNA molecule, said expression being indicative of stably plastid-transformed cells; and
   c) selecting cells expressing said phenotype, thereby obtaining said stably plastid-transformed cells of said multicellular plant.

2. The method of claim 1, wherein the transformation comprises bombardment of the cells of the multicellular plant with microprojectiles coated with the DNA molecule.

3. The method of claim 1, wherein said selectable marker sequence encodes said plastid 16S ribosomal RNA.

4. The method of claim 1, wherein said selectable marker sequence encodes a heterologous protein that inactivates spectinomycin or streptomycin.

5. The method of claim 1 wherein the plastids are chloroplasts.

6. The method of claim 1 wherein the plant is *Nicotiana tabacum*.

7. The method of claim 1 wherein the selectable phenotype is green pigmentation.

8. A plant cell obtained by the method of claim 1.

9. The method of claim 1, wherein said DNA molecule further comprises a foreign DNA of interest as said at least one additional DNA segment.

10. The plant cell obtained by the method of claim 9 wherein the foreign DNA of interest encodes a protein.

11. A method for obtaining a stably plastid-transformed multicellular plant, which comprises:
   a) transforming plastids of cells of said multicellular plant with a DNA molecule having:
      i) a targeting segment comprising a DNA sequence substantially homologous to a pre-determined sequence of a plastid genome, said targeting segment enabling insertion of said DNA molecule into said plastid genome by homologous recombination with said pre-determined sequence;
      ii) a selectable marker sequence disposed within said targeting segment, said selectable marker sequence being selected from the group consisting of: a sequence encoding a form of plastid 16S ribosomal RNA that is resistant to spectinomycin or streptomycin, and a sequence encoding a heterologous protein that inactivates spectinomycin or streptomycin, said selectable marker sequence conferring a selectable phenotype to cells having substantially all plastids transformed with said DNA molecule; and
      iii) at least one cloning site adapted for insertion of at least one additional DNA segment, said at least one cloning site being disposed within said targeting segment relative to said selectable marker sequence so as not to interfere with said conferring of said selectable phenotype;
   b) maintaining said cells in a selection medium which permits survival of cells having transformed or non-transformed plastids, and which further permits expression of said selectable phenotype in cells having substantially all plastids transformed with said DNA molecule, said expression being indicative of stably plastid-transformed cells; and
   c) selecting cells expressing said phenotype, thereby obtaining said stably plastid-transformed cells of said multicellular plant; and
   d) regenerating a plant from said stably plastid-transformed cells, thereby obtaining a stably plastid-transformed multicellular plant.

12. A multicellular plant obtained by the method of claim 11.

13. A multicellular plant the plastids of which have been stably transformed by a DNA molecule having:
   a) a targeting segment comprising a DNA sequence substantially homologous to a pre-determined sequence of a plastid genome, said targeting segment enabling insertion of said DNA molecule into said plastid genome by homologous recombination with said pre-determined sequence;
   b) a selectable marker sequence disposed within said targeting segment, said selectable marker sequence being selected from the group consisting of: a sequence encoding a form of plastid 16S ribosomal RNA that is resistant to spectinomycin or streptomycin, and a sequence encoding a heterologous protein that inactivates spectinomycin or streptomycin, said selectable marker sequence conferring a selectable phenotype to cells of said multicellular plant having substantially all plastids transformed with said DNA molecule; and
   c) a foreign DNA of interest disposed within said targeting segment relative to said selectable marker sequence so as not to interfere with said conferring of said selectable phenotype.

* * * * *